(12) United States Patent
Desenne et al.

(10) Patent No.: US 6,692,539 B2
(45) Date of Patent: Feb. 17, 2004

(54) COMPOSITION USEFUL FOR THE OXIDATION DYEING OF KERATIN FIBRES, CONTAINING AN OXYALKYLENATED CARBOXYLIC ACID ETHER, A NONIONIC SURFACTANT AND A PARTICULAR POLYMER

(75) Inventors: Patricia Desenne, Bois Colombres (FR); Cecile Bebot, Clichy (FR); Florence Laurent, Bois Colombres (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 10/323,769

(22) Filed: Dec. 20, 2002

(65) Prior Publication Data
US 2003/0172473 A1 Sep. 18, 2003

(30) Foreign Application Priority Data
Dec. 21, 2001 (FR) ............................................. 01 16738

(51) Int. Cl.[7] ................................................ A61K 7/13
(52) U.S. Cl. ........................ 8/405; 8/406; 8/407; 8/408; 8/421; 8/540; 8/547; 8/552; 8/554; 8/555
(58) Field of Search ............................ 8/405, 406, 407, 8/408, 421, 540, 547, 552, 554, 555

(56) References Cited

U.S. PATENT DOCUMENTS

2001/0023515 A1 * 9/2001 Cottard et al. ................. 8/406

* cited by examiner

Primary Examiner—Yogendra N. Gupta
Assistant Examiner—Eisa Elhilo
(74) Attorney, Agent, or Firm—Oblon, Spivak, McClelland, Maier & Neustadt, P.C.

(57) ABSTRACT

The invention relates to a composition useful for the oxidation dyeing of keratin fibers, in particular of human keratin fibers and more particularly the hair, containing, in a medium that is suitable for dyeing, at least one oxidation dye, at least one polyoxyalkylenated carboxylic acid ether or a salt thereof, at least one nonionic surfactant and at least one cationic or amphoteric polymer whose cationic charge density is greater than or equal to 2 meq/gram. The invention also relates to the dyeing devices and processes using the composition.

41 Claims, No Drawings

COMPOSITION USEFUL FOR THE OXIDATION DYEING OF KERATIN FIBRES, CONTAINING AN OXYALKYLENATED CARBOXYLIC ACID ETHER, A NONIONIC SURFACTANT AND A PARTICULAR POLYMER

BACKGROUND OF THE INVENTION

1. Field of the Invention

The present invention relates to a composition useful for the oxidation dyeing of keratin fibres, in particular of human keratin fibres and more particularly the hair, comprising, preferably in a medium that is suitable for dyeing, at least one oxidation dye, and also at least one polyoxyalkylenated carboxylic acid ether or a salt thereof, at least one nonionic surfactant and at least one cationic or amphoteric polymer whose cationic charge density is greater than or equal to 2 meq/gram.

The invention also relates to dyeing devices, kits, and processes using the composition.

2. Discussion of the Background

It is known practice to dye keratin fibres, and in particular human hair, with dye compositions containing oxidation dye precursors, generally known as "oxidation bases", in particular ortho- or para-phenylenediamines, ortho- or para-aminophenols, and heterocyclic bases.

Oxidation dye precursors are compounds that are initially uncoloured or only weakly coloured, which develop their dyeing power on the hair in the presence of oxidizing agents, leading to the formation of coloured compounds. The formation of these coloured compounds results either from an oxidative condensation of the "oxidation bases" with themselves or from an oxidative condensation of the "oxidation bases" with coloration modifiers, or "couplers", which are generally present in the dye compositions used in oxidation dyeing and are represented more particularly by meta-phenylenediamines, meta-aminophenols and meta-diphenols, and certain heterocyclic compounds.

The variety of molecules used, which consist on the one hand of the "oxidation bases" and on the other hand of the "couplers", allows a very wide range of colours to be obtained.

These oxidation bases and couplers are formulated in vehicles or supports allowing them to be applied to keratin fibres after mixing with an oxidizing agent.

These vehicles are generally aqueous and usually comprise one or more surfactants.

Thus, it has already been recommended to use fatty acids as anionic surfactant, in combination with a cationic or amphoteric polymer and a nonionic surfactant. The said combinations produce oxidation dye compositions that generate shades with very good dyeing properties. However, the search continues for supports that can further improve the properties of the colorations obtained.

SUMMARY OF THE INVENTION

Thus, after considerable research conducted in this matter, the inventors have now discovered that it is possible to obtain oxidation dye compositions that produce even more powerful and more chromatic shades, by introducing into the dye composition at least one polyoxyalkylenated carboxylic acid ether or a salt thereof, at least one nonionic surfactant and at least one cationic or amphoteric polymer whose cationic charge density is greater than or equal to 2 meq/gram.

DETAILED DESCRIPTION OF THE INVENTION

One subject of the present invention is thus a composition for the oxidation dyeing of keratin fibres, in particular of human keratin fibres and more particularly the hair, comprising, preferably in a medium that is suitable for dyeing, at least one oxidation dye, and wherein it also comprises at least one polyoxyalkylenated carboxylic acid ether or a salt thereof, at least one nonionic surfactant and at least one cationic or amphoteric polymer whose cationic charge density is greater than or equal to 2 meq/gram.

Another subject of the invention relates to a ready-to-use composition for the oxidation dyeing of keratin fibres, which comprises, preferably in a medium that is suitable for dyeing, at least one composition as described above and at least one oxidizing agent.

For the purposes of the present invention, the expression "ready-to-use composition" means the composition intended to be applied immediately to the keratin fibres, i.e. it may be stored before use without further modification, or may result from the extemporaneous mixing of two or more compositions.

The invention is also directed towards a process for the oxidation dyeing of keratin fibres, and in particular of human keratin fibres such as the hair, which consists in applying to the fibres a dye composition comprising, in a medium that is suitable for dyeing, at least one oxidation dye, the colour being developed at alkaline, neutral or acidic pH using an oxidizing composition comprising, in a medium that is suitable for dyeing, at least one oxidizing agent, which is mixed with the dye composition just at the time of use, or which is applied sequentially without intermediate rinsing, the dye composition and the oxidizing composition also comprising, distributed indifferently between the two, at least one polyoxyalkylenated carboxylic acid ether or a salt thereof, at least one nonionic surfactant and at least one cationic or amphoteric polymer whose cationic charge density is greater than or equal to 2 meq/gram.

In one variant of the process, the polyoxyalkylenated carboxylic acid ether(s) or salts thereof, nonionic surfactant(s) and cationic or amphoteric polymer(s) whose cationic charge density is greater than or equal to 2 meq/gram are combined in the same dye composition or oxidizing composition and even more particularly in the dye composition.

A subject of the invention is also a multi-compartment dyeing device or "kit" for the oxidation dyeing of keratin fibres, in particular of human keratin fibres and more particularly the hair, which comprises a compartment containing a dye composition comprising, in a medium that is suitable for dyeing, at least one oxidation dye, and another compartment containing an oxidizing composition comprising, in a medium that is suitable for dyeing, an oxidizing agent, the dye composition and the oxidizing composition also comprising, distributed indifferently between the two, at least one polyoxyalkylenated carboxylic acid ether, at least one nonionic surfactant and at least one cationic or amphoteric polymer whose cationic charge density is greater than or equal to 2 meq/gram.

In one device variant, the polyoxyalkylenated carboxylic acid ether(s) or salts thereof, nonionic surfactant(s) and cationic or amphoteric polymer(s) whose cationic charge density is greater than or equal to 2 meq/gram are combined in the same dye composition or oxidizing composition, and even more particularly in the dye composition.

However, other characteristics, aspects, subjects and advantages of the invention will emerge even more clearly on reading the description and the examples that follow.

Polyoxyalkylenated carboxylic acid ethers and salts thereof The expression "polyoxyalkylenated carboxylic acid ether or salt thereof" preferably means any compound of formula (I) below:

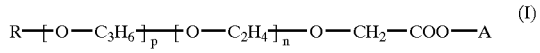

in which:

R represents a linear or branched $C_8$–$C_{22}$ alkyl or alkenyl radical or mixture of radicals, a ($C_8$–$C_9$)alkylphenyl radical or a radical R"CONH-$CH_2$—$CH_2$- with R' denoting a linear or branched $C_{11}$–$C_{21}$, alkyl or alkenyl radical, n is an integer or fraction ranging from 2 to 24, p is an integer or fraction ranging from 0 to 6, A denotes a hydrogen atom or Na, K, Li, ½ Mg or a monoethanolamine, ammonium or triethanolamine residue.

The polyoxyalkylenated carboxylic acid ethers and salts thereof preferably used according to the present invention are selected from the group consisting of those of formula (I) in which R denotes a ($C_{12}$–$C_{14}$)alkyl, oleyl, cetyl or stearyl radical or mixture of radicals; a nonylphenyl or octylphenyl radical, A denotes a hydrogen or sodium atom, p=0, and n ranges from 2 to 20 and preferably from 2 to 10.

Compounds of formula (I) in which R denotes a ($C_{12}$) alkyl radical, A denotes a hydrogen or sodium atom, p=0 and n ranges from 2 to 10 are even more preferably used.

Among the commercial products that may preferably be used are the products sold by the company Chem Y under the names:

Akypo® NP 70 (R=nonylphenyl, n=7, p=0, A=H)
Akypo® NP 40 (R=nonylphenyl, n=4, p=0, A=H)
Akypo® OP 40 (R=octylphenyl, n=4, p=0, A=H)
Akypo® OP 80 (R=octylphenyl, n=8, p=0, A=H)
Akypo® OP 190 (R=octylphenyl, n=19, p=0, A=H)
Akypo® RLM 38 (R=($C_{12}$–$C_{14}$)alkyl, n=3.8, p=0, A=H)
Akypo® RLM 38 NV (R=($C_{12}$–$C_{14}$)alkyl, n=4, p=0, A=Na)
Akypo® RLM 45 (R=($C_{12}$–$C_{14}$)alkyl, n=4.5, p=0, A=H)
Akypo® RLM 45 NV (R=($C_{12}$–$C_{14}$)alkyl, n=4.5, p=0, A=Na)
Akypo® RLM 100 (R=($C_{12}$–$C_{14}$)alkyl, n=10, p=0, A=H)
Akypo® RLM 100 NV (R=($C_{12}$–$C_{14}$)alkyl, n=10, p=0, A=Na)
Akypo® RLM 130 (R=($C_{12}$–$C_{14}$)alkyl, n=13, p=0, A=H)
Akypo® RLM 160 NV (R=($C_{12}$–$C_{14}$)alkyl, n=16, p=0, A=Na)
Akypo® RO 20(R=oleyl,n=2,p=0,A=H)
Akypo® RO 90(R=oleyl,n=9,p=0, A=H)
Akypo® RCS 60 (R=cetyl/stearyl, n=6, p=0,A=H)
Akypo® RS 60 (R=stearyl, n=6, p=0, A=H)
Akypo® RS 100 (R=stearyl, n=10, p=0, A=H)
Akypo® RO 50 (R=oleyl, n=5, p=0, A=H),
or by the company Sandoz under the names:
Sandopan ACA-48 (R=cetyl/stearyl, n=24, p=0, A=H)
Sandopan DTC-Acid (R=($C_{13}$)alkyl, n=6, p=0, A=H)
Sandopan DTC (R=($C_{13}$)alkyl, n=6, p=0, A=Na)
Sandopan LS 24 (R=($C_{12}$–$C_{14}$)alkyl, n=12, p=0, A=Na)
Sandopan JA 36 (R =($C_{13}$)alkyl, n=18, p=0, A=H),
and more particularly the products sold under the following names:
Akypo® NP 70
Akypo® NP 40
Akypo® OP 40
Akypo® OP 80
Akypo® RLM 25
Akypo® RLM 45

Akypo® RLM 100
Akypo® RO 20
Akypo® RO 50
Akypo® RLM 38.

The polyoxyalkylenated carboxylic acid ethers or salts thereof may represent from about 2% to 15% and preferably from about 3% to 10% of the total weight of the dye composition, and from about 0.5% to 15% and preferably from about 0.7% to 10% of the total weight of the ready-to-use dye composition (comprising the oxidizing agent).

Nonionic surfactants

The nonionic surfactants useful herein are compounds themselves well known per se (see in particular in this regard "Handbook of Surfactants" by M. R. PORTER, Blackie & Son publishing (Glasgow and London), 1991, pp. 116–178).

Thus, they may be chosen in particular from (nonlimiting list) alcohols, alpha-diols, polyethoxylated or polypropoxylated alkylphenols having a fatty chain containing, for example, from 8 to 22 carbon atoms, it being possible for the number of ethylene oxide or propylene oxide groups to range in particular from 1 to 50. Mention may also be made of copolymers of ethylene and propylene oxide, condensates of ethylene and propylene oxide with fatty alcohols; polyethoxylated fatty amides preferably having from 2 to 30 mol of ethylene oxide, mono- or polyglycerolated fatty alcohols containing on average 1 to 30 glycerol groups and polyglycerolated fatty amides containing on average 1 to 5 glycerol groups and in particular 1.5 to 4; oxyethylenated fatty acid esters of sorbitan having from 2 to 30 mol of ethylene oxide; fatty acid esters of sucrose, fatty acid esters of polyethylene glycol, alkyl polyglycosides, N-alkylglucamine derivatives, amine oxides such as oxides of alkyl ($C_{10}$–$C_{14}$)amines or oxides of N-acylaminopropylmorpholine.

According to the invention, it is preferable to use:

1) fatty alcohols containing from 8 to 22 carbon atoms and oxyethylenated with 1 to 10 mol of ethylene oxide (1 to 10 EO). Among them, there may be mentioned more particularly lauryl alcohol 2 EO, lauryl alcohol 3 EO, decyl alcohol 3 EO and decyl alcohol 5 EO.

2) mono- or polyglycerolated fatty alcohols which may be represented by the formula (II) below:

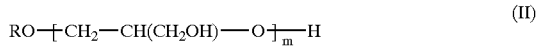

in which:

R represents a saturated or unsaturated, linear or branched radical containing from 8 to 40 carbon atoms and preferably from 10 to 30 carbon atoms;

m represents a number ranging from 1 to 30 and preferably from 1 to 10.

Compounds of this type that may be mentioned include lauryl alcohol containing 4 mol of glycerol (INCI name: Polyglyceryl-4 Lauryl Ether), lauryl alcohol containing 1.5 mol of glycerol, oleyl alcohol containing 4 mol of glycerol (INCI name: Polyglyceryl-4 Oleyl Ether), oleyl alcohol containing 2 mol of glycerol (INCI name: Polyglyceryl-2 Oleyl Ether), cetearyl alcohol containing 2 mol of glycerol, cetearyl alcohol containing 6 mol of glycerol, oleocetyl alcohol containing 6 mol of glycerol, and octadecanol containing 6 mol of glycerol.

The fatty alcohol may represent a mixture of fatty alcohols in the same respect that the value of m represents a random value, which means that several species of polyglycerolated fatty alcohols may coexist in a commercial product in the form of a mixture.

Among the mono- or polyglycerolated fatty alcohols that it is more particularly preferred to use are the $C_8/C_{10}$ alcohol containing one mole of glycerol, the $C_{10}/C_{12}$ alcohol containing 1 mol of glycerol and the $C_{12}$ alcohol containing 1.5 mol of glycerol.

The nonionic surfactant(s) represent(s) from 2% to 40% approximately and preferably from 4% to 20% approximately of the total weight of the dye composition, and from 0.5% to 40% approximately and preferably from 1% to 20% approximately of the total weight of the ready-to-use dye composition (comprising the oxidizing agent).

Cationic or amphoteric polymers

The cationic or amphoteric polymers according to the present invention preferably have a cationic charge density greater than or equal to 2 meq per gram.

The charge density may be determined according to the Kjeldahl method. It is generally measured at a pH of 3.9.

The Kjeldahl method is well known to persons skilled in the art and is for example described, for the micro-Kjeldahl in:

AACC: Approved methods of the American Association of Cereal Chemists, 9th ed., St Paul, Minn. (1995), AOAC: Official methods of analysis of AOAC International, 16th ed., Arlington, Va. (1995), and for the semimicro-Kjeldahl in:

Vogel A.I: Elementary practical organic chemistry Part 3 "Quantitative Organic Analysis", Longman Group.

The cationic polymers having a cationic charge density greater than or equal to 2 meq per gram may be preferably selected from the group consisting of:

(1) quaternary polymers of vinylpyrrolidone and of vinylimidazole such as, for example, the products marketed under the names Luviquat FC 905®, FC 550® and FC 370® by the company BASF.

(2) homopolymers and copolymers containing, in the chain, units of formula (III) below:

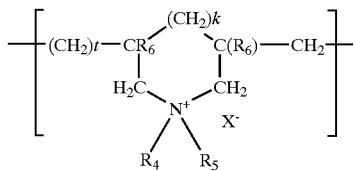

(III)

in which k and t are equal to 0 or 1, the sum k+t being equal to 1;

$R_4$ and $R_5$, which are identical or different, denote an alkyl group having from 1 to 8 carbon atoms, a ($C_1$–$C_5$) hydroxyalkyl group, a ($C_1$–$C_4$) amidoalkyl group, or $R_4$ and $R_5$ denote together with the nitrogen atom to which they are attached a piperidyl or morpholinyl group;

$R_6$ denotes a hydrogen atom or a methyl radical;

$X^-$ is an anion.

Preferably, $R_4$ and $R_5$, which are identical or different, denote an alkyl group having from 1 to 4 carbon atoms; $X^-$ is a bromide, chloride, acetate, borate, citrate, tartrate, bisulphate, bisulphite, sulphate or phosphate anion.

Such polymers are in particular described in French patent 2,080,759 and in its certificate of addition 2,190,406.

Among them, mention may be made more particularly of the dimethyldiallylammonium chloride homopolymer (POLYQUATERNIUM 6) sold under the name "Merquat® 100" by the company Calgon and its homologues of low weight-average molecular mass and the copolymers of dimethyldiallylammonium chloride and acrylamide marketed under the name "Merquat® 550".

(3) quaternary diammonium polymers containing repeating units of formula (IV) below:

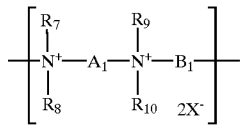

(IV)

in which:

$R_7$, $R_8$, $R_9$ and $R_{10}$, which are identical or different, represent aliphatic, alicyclic or arylaliphatic radicals containing from 1 to 20 carbon atoms or lower hydroxyalkylaliphatic radicals, or alternatively $R_7$, $R_8$, $R_9$ and $R_{10}$, together or separately, constitute with the nitrogen atoms to which they are attached heterocycles optionally containing a second heteroatom other than nitrogen, or alternatively $R_7$, $R_8$, $R_9$ and $R_{10}$ represent a linear or branched $C_1$–$C_6$ alkyl radical substituted with a nitrile, ester, acyl, amide group or a group —CO—O—$R_{11}$—D or —CO—NH—$R_{11}$—D in which $R_{11}$ is an alkylene and D a quaternary ammonium group;

$A_1$ and $B_1$ represent polymethylene groups containing from 2 to 20 carbon atoms which are linear or branched, saturated or unsaturated, and which may contain, linked to or intercalated in the main chain, one or more aromatic rings or one or more oxygen or sulphur atoms or sulphoxide, sulphone, disulphide, amino, alkylamino, hydroxyl, quaternary ammonium, ureido, amide or ester groups, and $X^-$ is an anion;

$A_1$, $R_7$ and $R_9$ can form with the two nitrogen atoms to which they are attached a piperazine ring; in addition, if $A_1$ denotes a linear or branched, saturated or unsaturated alkylene or hydroxyalkylene radical, $B_1$ can also denote a group —$(CH_2)_n$—CO—D—OC—$(CH_2)_n$—in which n is between 1 and 100 and preferably between 1 and 50, and D denotes:

a) a glycol residue of formula: —O—Z—O—, where Z denotes a linear or branched hydrocarbon radical or a group corresponding to one of the following formulae:

—$(CH_2$—$CH_2$—$O)_x$—$CH_2$—$CH_2$—

—$[CH_2$—$CH(CH_3)$—$O]_y$—$CH_2$—$CH(CH_3)$— where x and y denote an integer from 1 to 4, representing a defined and unique degree of polymerization, or any number from 1 to 4, representing an average degree of polymerization;

b) a bis-secondary diamine residue such as a piperazine derivative;

c) a bis-primary di amine residue of formula: —NH—Y—NH—, where Y denotes a linear or branched hydrocarbon radical, or alternatively the divalent radical

—$CH_2$—$CH_2$—S—S—$CH_2$—$CH_2$—;

d) a ureylene group of formula: —NH—CO—NH—.

The cationic polymers containing units of formula (IV) have a number-average molecular mass generally between 1000 and 100000.

In these polymers, $X^-$ is a chloride or bromide anion.

Polymers of this type are described in particular in French patents 2,320,330, 2,270,846, 2,316,271, 2,336,434 and 2,413,907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

It is more particularly possible to use, among them, the polymers which consist of repeating units corresponding to the following formula (IV)a:

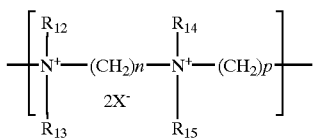

(IV)a in which $R_{12}$, $R_{13}$, $R_{14}$ and $R_{15}$, which are identical or different, denote an alkyl or hydroxyalkyl radical having from about 1 to 4 carbon atoms, n and p are integers varying from 2 to 20.

Still more particularly, the compounds of formula (VI) in which $R_{12}$, $R_{13}$, $R_{14}$ and $R_{15}$ represent a methyl or ethyl radical are preferred.

Particularly preferred cationic polymers of formula (VI) are those for which $R_{12}$, $R_3$, $R_{14}$ and $R_{15}$ represent a methyl radical and n=3, p=6 and X=Cl, and in particular those whose molecular weight, determined by gel permeation chromatography, is between 9 500 and 9 900 [polymer W].

Other cationic polymers of formula (VI) which are particularly preferred are those for which $R_{12}$ and $R_{13}$ represent a methyl radical, $R_{14}$ and $R_{15}$ represent an ethyl radical and n=p=3 and X=Br, and in particular those whose molecular weight, determined by gel permeation chromatography, is about 1200 [polymer U].

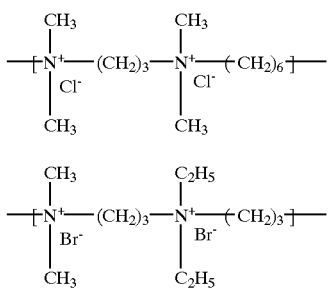

The said polymers with units (W) and (U) are prepared and described in French patent 2 270 846.

(4) quaternary diammonium polymers consisting of units of formula (V) below:

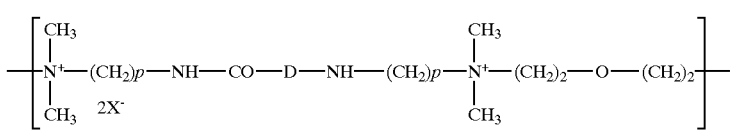

in which:
p denotes an integer varying from about 1 to 6,
D may be zero or may represent a group —$(CH_2)_r$—CO— in which r denotes a number equal to 4 or to 7, and
X⁻ is an anion.

The cationic polymers containing units of formula (V) are in particular described in patent application EP-A-122 324.

Among these polymers, those preferred have a molecular mass, measured by carbon 13 NMR, of less than 100 000, and in whose formula:
p denotes an integer varying from about 1 to 6,
D may be zero or may represent a group —$(CH_2)_r$—CO— in which r denotes a number equal to 4 or to 7, and X⁻ is an anion derived from an inorganic or organic acid.

Among the said polymers with units of formula (V), preference is also given to those for which p is equal to 3, and a) D represents a group —$(CH_2)_4$—CO—, X denotes a chlorine atom, the molecular mass, measured by carbon 13 NMR ($^{13}C$ NMR), being about 5 600; a polymer of this type is proposed by the company Miranol under the name Mirapol-AD1, b) D represents a group —$(CH_2)_7$—CO—, X denotes a chlorine atom, the molecular mass, measured by carbon 13 NMR ($^{31}C$ NMR), being about 8 100; a polymer of this type is proposed by the company Miranol under the name Mirapol-AZ1, c) D denotes the value zero, X denotes a chlorine atom, the molecular mass, measured by carbon 13 NMR ($^{13}C$ NMR), being about 25 500; a polymer of this type is sold by the company Miranol under the name Mirapol-A15, d) a block copolymer formed of units corresponding to the polymers described in paragraphs a) and c), proposed by the company Miranol under the names Mirapol-9, (molecular mass $^{13}C$ NMR, about 7 800) Mirapol-175, (molecular mass $^{13}C$ NMR, about 8 000) Mirapol-95, (molecular mass $^{13}C$ NMR, about 12 500). Still more particularly, preference is given according to the invention to the polymer with units of formula (V) in which p is equal to 3, D denotes the value zero, X denotes a chlorine atom, the molecular mass, measured by carbon 13 NMR ($^{13}C$ NMR), being about 25 500.

The said cationic polymers with units of formula (V) may be prepared according to the methods described in U.S. Pat. Nos. 4,157,388, 4,390,689, 4,702,906, 4,719,282.

Preferable amphoteric polymers are polymers containing units K and M randomly distributed in the polymer chain, in which K denotes a unit derived from a monomer containing at least one basic nitrogen atom and M denotes a unit derived from an acidic monomer containing one or more carboxylic or sulphonic groups, or alternatively K and M can denote groups derived from carboxybetaine or sulphobetaine zwitterionic monomers;

K and M can also denote a cationic polymer chain containing primary, secondary, tertiary or quaternary amine groups in which at least one of the amine groups bears a carboxylic or sulphonic group connected via a hydrocarbon radical, or alternatively K and M form part of a polymer chain containing an α,β-dicarboxylic ethylene unit in which one of the carboxylic groups has been made to react with a polyamine containing one or more primary or secondary amine groups.

The amphoteric polymers corresponding to the definition given above and satisfying the cationic charge density ≧2 meq/g which are more particularly preferred according to the invention are selected from the group consisting of the copolymers of acrylic acid and dimethyldiallylammonium proposed under the names Merquat® 280, Merquat® 295 and Merquat® Plus 3330 by the company Calgon.

The cationic and amphoteric polymers having a cationic charge density greater than or equal to 2 meq per gram preferably represent about 0.01% to 10% by weight and more preferably from about 0.2% to 5% by weight, relative to the total weight of the dye composition and preferably from about 0.0025% to 10% and more preferably from about 0.05% to 5% of the total weight of that which is ready to use (comprising the oxidizing agent).

Oxidation dyes

The oxidation dyes that may be used according to the invention are preferably selected from the group consisting of oxidation bases and/or couplers.

The compositions according to the invention preferably contain at least one oxidation base.

The oxidation bases that may be used in the context of the present invention are preferably selected from the group consisting of those conventionally used in oxidation dyeing, and among which mention may be made especially of ortho- and para-phenylenediamines, double bases, ortho- and para-aminophenols, the heterocyclic bases below, and also the addition salts thereof with an acid.

Mention may be made especially of:

(I) the para-phenylenediamines of formula (VII) below, and the addition salts thereof with an acid:

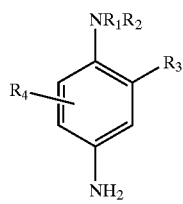

(VII)

in which:

$R_1$ represents a hydrogen atom, a $C_1$–$C_4$ alkyl radical, a $C_1$–$C_4$ monohydroxyalkyl radical, a $C_2$–$C_4$ polyhydroxyalkyl radical, a ($C_1$–$C_4$)alkoxy($C_1$–$C_4$)alkyl radical or a $C_1$–$C_4$ alkyl radical substituted with a nitrogenous, phenyl or 4'-aminophenyl group;

$R_2$ represents a hydrogen atom, a $C_1$–$C_4$ alkyl radical, a $C_1$–$C_4$ monohydroxyalkyl radical, a $C_2$–$C_4$ polyhydroxyalkyl radical, a ($C_1$–$C_4$)alkoxy($C_1$–$C_4$)alkyl radical or a $C_1$–$C_4$ alkyl radical substituted with a nitrogenous group;

$R_1$ and $R_2$ may also form, with the nitrogen atom that bears them, a 5- or 6-membered nitrogen heterocycle optionally substituted with one or more alkyl, hydroxyl or ureido groups;

$R_3$ represents a hydrogen atom, a halogen atom such as a chlorine atom, a $C_1$–$C_4$ alkyl radical, a sulpho radical, a carboxyl radical, a $C_1$–$C_4$ monohydroxyalkyl radical, a $C_1$–$C_4$ hydroxyalkoxy radical, an acetylamino($C_1$–$C_4$) alkoxy radical, a mesylamino($C_1$–$C_4$)alkoxy radical or a carbamoylamino($C_1$–$C_4$)alkoxy radical, $R_4$ represents a hydrogen or halogen atom or a $C_1$–$C_4$ alkyl radical.

Among the nitrogenous groups of formula (VII) above, mention may be made especially of amino, mono($C_1$–$C_4$) alkylamino, di($C_1$–$C_4$)alkylamino, tri($C_1$–$C_4$)alkylamino, monohydroxy($C_1$–$C_4$)alkylamino, imidazolinium and ammonium radicals.

Among the para-phenylenediamines of formula (VII) above, mention may be made more particularly of para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(-hydroxyethyl)-para-phenylenediamine, 4-amino-N,N-bis(-hydroxyethyl)-2-methylaniline, 4-amino-N,N-bis(-hydroxyethyl)-2-chloroaniline, 2-hydroxyethyl-para-phenylenediamine, 2-fluoro-para-phenylenediamine, 2-isopropyl-para-phenylenediamine, N-(-hydroxypropyl)-para-phenylenediamine, 2-hydroxymethyl-para-phenylenediamine, N,N-dimethyl-3-methyl-para-phenylenediamine, N-ethyl-N-(-hydroxyethyl)-para-phenylenediamine, N-(γ-dihydroxypropyl)-para-phenylenediamine, N-(4'-aminophenyl)-para-phenylenediamine, N-phenyl-para-phenylenediamine and 2-hydroxyethyloxy-para-phenylenediamine, 2—acetylaminoethyloxy-para-phenylenediamine, N-(-methoxyethyl)-para-phenylenediamine, 2-methyl-1-N-hydroxyethyl-para-phenylenediamine and N-(4-aminophenyl)-3-hydroxypyrrolidine, and the addition salts thereof with an acid.

Among the para-phenylenediamines of formula (VII) above, para-phenylenediamine, para-tolylenediamine, 2-isopropyl-para-phenylenediamine, 2—hydroxyethyl-para-phenylenediamine, 2-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(-hydroxyethyl)-para-phenylenediamine and 2-chloro-para-phenylenediamine, and the addition salts thereof with an acid, are most particularly preferred.

(II) According to the invention, the term double bases means compounds containing at least two aromatic nuclei bearing amino and/or hydroxyl groups.

Among the double bases that can be used as oxidation bases in the dye compositions in accordance with the invention, mention may be made especially of the compounds corresponding to formula (VIII) below, and the addition salts thereof with an acid:

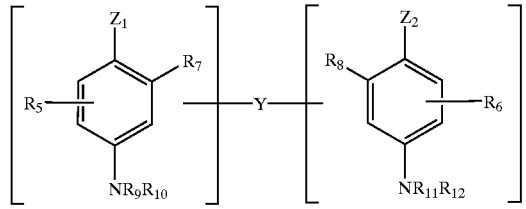

(VIII)

in which:

$Z_1$ and $Z_2$, which may be identical or different, represent a hydroxyl or -NH2 radical which may be substituted with a $C_1$–$C_4$ alkyl radical or with a linker arm Y;

the linker arm Y represents a linear or branched alkylene chain containing from 1 to 14 carbon atoms, which may be interrupted by or terminated with one or more nitrogenous groups and/or one or more hetero atoms such as oxygen, sulphur or nitrogen atoms, and optionally substituted with one or more hydroxyl or $C_1$–$C_6$ alkoxy radicals;

$R_5$ and $R_6$ represent a hydrogen or halogen atom, a $C_1$–$C_4$ alkyl radical, a $C_1$–$C_4$ monohydroxyalkyl radical, a $C_2$–$C_4$ polyhydroxyalkyl radical, a $C_1$–$C_4$ aminoalkyl radical or a linker arm Y;

$R_7$, $R_8$, $R_9$, $R_{10}$, $R_{11}$ and $R_{12}$, which may be identical or different, represent a hydrogen atom, a linker arm Y or a $C_1$–$C_4$ alkyl radical;

it being understood that the compounds of formula (VIII) contain only one linker arm Y per molecule.

Among the nitrogenous groups of formula (VIII) above, mention may especially be made of amino, mono($C_1$–$C_4$)

alkylamino, di($C_1$–$C_4$)alkylamino, tri($C_1$–$C_4$)alkylamino, monohydroxy($C_1$–$C_4$)alkylamino, imidazolinium and ammonium radicals.

Among the double bases of formula (VIII) above, mention may be made more particularly of N,N'-bis(-hydroxyethyl)-N,N'-bis(4 '-aminophenyl)-1,3-diaminopropanol, N,N'-bis(-hydroxyethyl)-N,N'-bis(4'-aminophenyl)ethylenediamine, N,N'-bis(4-aminophenyl)tetramethylenediamine, N,N'-bis(-hydroxyethyl)-N,N'-bis(4-aminophenyl)-tetramethylenediamine, N,N'-bis(4-methylaminophenyl)tetramethylenediamine, N,N'-bis-(ethyl)-N,N '-bis(4'-amino-3 '-methylphenyl) ethylenediamine and 1,8-bis(2,5 -diaminophenoxy)-3,5-dioxaoctane, and the addition salts thereof with an acid.

Among these double bases of formula (VIII), N,N'-bis(-hydroxyethyl)-N,N'-bis(4'-aminophenyl)-1,3-diaminopropanol and 1,8-bis(2,5-diaminophenoxy)-3,5-dioxaoctane, or one of the addition salts thereof with an acid, are particularly preferred.

(III) The para-aminophenols corresponding to formula (IX) below, and the addition salts thereof with an acid:

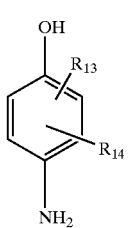

(IX)

in which:

$R_{13}$ represents a hydrogen atom, a halogen atom such as fluorine, or a $C_1$–$C_4$ alkyl, $C_1$–$C_4$ monohydroxyalkyl, ($C_1$–$C_4$)alkoxy($C_1$–$C_4$)alkyl, $C_1$–$C_4$ aminoalkyl or hydroxy ($C_1$ –$C_4$)alkylamino($C_1$–$C_4$)alkyl radical, $R_{14}$ represents a hydrogen atom, a halogen atom such as fluorine, or a Cl-$C_4$-alkyl, $C_1$–$C_4$ monohydroxyalkyl, $C_2$–$C_4$ polyhydroxyalkyl, $C_1$–$C_4$ aminoalkyl, $C_1$–$C_4$ cyanoalkyl or ($C_1$–$C_4$)alkoxy-($C_1$–$C_4$)alkyl radical.

Among the para-aminophenols of formula (IX) above, mention may be made more particularly of para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol and 4-amino-2-(-hydroxyethylaminomethyl)phenol, and the addition salts thereof with an acid.

(IV) The ortho-aminophenols that can be used as oxidation bases in the context of the present invention are chosen especially from 2-aminophenol, 2-amino-1-hydroxy-5-methylbenzene, 2-amino-1-hydroxy-6-methylbenzene and 5-acetamido-2-aminophenol, and the addition salts thereof with an acid.

(V) Among the heterocyclic bases that can be used as oxidation bases in the dye compositions in accordance with the invention, mention may be made more particularly of pyridine derivatives, pyrimidine derivatives and pyrazole derivatives, and the addition salts thereof with an acid.

Among the pyridine derivatives, mention may be made more particularly of the compounds described, for example, in patents GB 1 026 978 and GB 1 153 196, such as 2,5-diaminopyridine, 2-(4-methoxyphenyl)amino-3-aminopyridine, 2,3-diamino-6-methoxypyridine, 2-(-methoxyethyl)amino-3-amino-6-methoxypyridine and 3,4-diaminopyridine, and the addition salts thereof with an acid.

Among the pyrimidine derivatives, mention may be made more particularly of the compounds described, for example, in German patent DE 2 359 399 or Japanese patents JP 88-169 571 and JP 91-10659 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and pyrazolopyrimidine derivatives such as those mentioned in patent application FR-A-2 750 048 and among which mention may be made of pyrazolo[1,5-a]pyrimidine-3,7-diamine; 2,5-dimethylpyrazolo[1,5-a]pyrimidine-3,7-diamine; pyrazolo [1,5-a]pyrimidine-3,5-diamine; 2,7-dimethylpyrazolo[1,5-a]pyrimidine-3,5-diamine; 3-aminopyrazolo[1,5-a] pyrimidin-7-ol; 3-aminopyrazolo[1,5-a]pyrimidin-5-ol; 2-(3-aminopyrazolo[ 1,5-a]pyrimidin-7-ylamino)ethanol; 2-(7-aminopyrazolo[1,5-a]pyrimidin-3-ylamino)ethanol; 2-[(3-aminopyrazolo[1,5-a]pyrimidin-7-yl)(2-hydroxyethyl)amino]ethanol, 2-[(7-aminopyrazolo[1,5-a] pyrimidin-3-yl)(2-hydroxyethyl)amino]ethanol; 5,6-dimethylpyrazolo[1,5-a]pyrimidine-3,7-diamine; 2,6-dimethylpyrazolo[1,5-a]pyrimidine-3,7-diamine; 2,5,N7, N7-tetramethylpyrazolo[1,5-a]pyrimidine-3,7-diamine and 3-amino-S-methyl-7-imidazolylpropylamino-pyrazolo[1,5-a]pyrimidine and the addition salts thereof and the tautomeric forms thereof, when a tautomeric equilibrium exists, and the addition salts thereof with an acid.

Among the pyrazole derivatives, mention may be made more particularly of the compounds described in patents DE 3 843 892, DE 4 133 957 and patent applications WO 94/08969, WO 94/08970, FR-A-2 733 749 and DE 195 43 988, such as 4,5-diamino-1-methylpyrazole, 3,4-diaminopyrazole, 4,5-diamino-1-(4'-chlorobenzyl)pyrazole, 4,5-diamino-1,3-dimethylpyrazole, 4,5 -diamino-3 -methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-(-hydroxyethylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3 -methyl-1-isopropylpyrazole, 4-amino-5 -(2'-aminoethyl)amino-1,3 -dimethyl-pyrazole, 3,4,5-triaminopyrazole, 1-methyl-3, 4,5-triaminopyrazole, 3,5-diamino-1-methyl-4-methylaminopyrazole and 3,5-diamino-4-(β-hydroxyethyl) amino-1-methylpyrazole, and the addition salts thereof with an acid.

According to the present invention, the oxidation bases preferably represent from about 0.0005% to 12% by weight relative to the total weight of the composition not comprising the oxidizing agent, and even more preferably from about 0.005% to 8% by weight relative to this weight.

The couplers that may be used in the dye composition according to the invention include those conventionally used in oxidation dye compositions, including meta-aminophenols, meta-phenylenediamines and meta-diphenols, naphthols and heterocyclic couplers such as, for example, indole derivatives, indoline derivatives, sesamol and its derivatives, pyridine derivatives, pyrazolotriazole derivatives, pyrazolones, indazoles, benzimidazoles, benzothiazoles, benzoxazoles, 1,3-benzodioxoles and quinolines, and the addition salts thereof with an acid.

These couplers may be chosen more particularly from 2,4-diamino-1-(-hydroxyethyloxy)benzene, 2-methyl-5- aminophenol, 5-N-(-hydroxyethyl)amino-2-methylphenol, 3-aminophenol, 1,3-dihydroxybenzene, 1,3-dihydroxy-2-methylbenzene, 4-chloro-1,3-dihydroxybenzene, 2-amino-4-(-hydroxyethylamino)-1-methoxybenzene, 1,3-diaminobenzene, 1,3-bis(2,4-diaminophenoxy)propane, sesamol, 1-amino-2-methoxy-4,5-methylenedioxybenzene, α-naphthol, 6-hydroxyindole, 4-hydroxyindole, 4-hydroxy-N—hydroxyethylindole, 6-hydroxyindoline, 2,6-dihydroxy-4-methylpyridine, 1H-3-methylpyrazol-5-one, 1-phenyl-3-methylpyrazol-5-one, 2-amino-3-hydroxypyridine, 3,6-dimethylpyrazolo[3,2-c]-1,2,4-triazole and 2,6-dimethylpyrazolo[1,5-b]-1,2,4-triazole, and the addition salts thereof with an acid.

When they are present, these couplers preferably represent from about 0.0001% to 10% by weight relative to the total weight of the composition not comprising the oxidizing agent, and even more preferably from about 0.005% to 5% by weight.

In general, the addition salts with an acid of the oxidation bases and couplers are chosen preferably from the hydrochlorides, hydrobromides, sulphates, tartrates, lactates and acetates.

The dye composition in accordance with the invention may also comprise one or more direct dyes, especially to modify the shades or to enrich them with glints. These direct dyes include those selected from the group consisting of neutral, cationic or anionic nitro dyes, azo dyes or anthraquinone dyes, conventionally used or those described especially in patent applications FR-2 782 450, 2 782 451, 2 782 452 and EP-1 025 834, in a weight proportion from about 0.001% to 20% and preferably from 0.01% to 10% of the total weight of the composition.

The ready-to-use composition according to the invention may also comprise in the dye composition and/or the oxidizing composition agents for adjusting the rheology, such as fatty acid amides optionally oxyethylenated (coconut monoethanolamide or diethanolamide, oxyethylenated carboxylic acid alkyl ether monoethanolamide), cellulose thickeners (hydroxyethylcellulose, hydroxypropylcellulose, carboxymethylcellulose, etc.), guar gum and its derivatives (hydroxypropyl guar, etc.), gums of microbial origin (xanthan gum, scleroglucan gum, etc.), crosslinked homopolymers of acrylic acid or of acrylamidopropanesulphonic acid, and associative polymers as described below.

Associative polymers that may be used according to the invention

Associative polymers are water-soluble polymers capable, in an aqueous medium, of reversibly associating together or with other molecules.

Their chemical structure comprises hydrophilic zones and hydrophobic zones characterized by at least one fatty chain.

The associative polymers according to the invention may be of anionic, cationic or amphoteric type, and preferably of nonionic or cationic type.

Their weight concentration in the dye composition can range from about 0.01% to 10% of the total weight of the composition, and in the ready-to-use composition (comprising the oxidizing agent), from about 0.0025% to 10% of the total weight of the composition. More preferably, this amount ranges from about 0.1% to 5% by weight in the dye composition and from about 0.025% to 10% in the ready-to-use composition.

Associative polymers of anionic type:

Particular mention may be made of:

(I) those comprising at least one hydrophilic unit and at least one fatty-chain allyl ether unit, more particularly those whose hydrophilic unit consists of an ethylenic unsaturated anionic monomer, more particularly a vinylcarboxylic acid and most particularly an acrylic acid or a methacrylic acid or mixtures thereof, the fatty-chain allyl ether unit of which corresponding to the monomer of formula (I) below:

$$CH_2=CR'CH_2OB_nR \quad \text{(I)}$$

in which R' denotes H or $CH_3$, B denotes an ethyleneoxy radical, n is zero or denotes an integer ranging from 1 to 100, R denotes a hydrocarbon-based radical selected from the group consisting of alkyl, arylalkyl, aryl, alkylaryl and cycloalkyl radicals, containing from 8 to 30 carbon atoms, preferably 10 to 24 carbon atoms and even more particularly from 12 to 18 carbon atoms. A unit of formula (I) that is more particularly preferred is a unit in which R' denotes H, n is equal to 10 and R denotes a stearyl ($C_{18}$) radical.

Anionic associative polymers of this type are described and prepared, according to an emulsion polymerization process, in patent EP-0 216 479.

Among these anionic associative polymers that are particularly preferred according to the invention are polymers formed from 20% to 60% by weight of acrylic acid and/or of methacrylic acid, from 5% to 60% by weight of lower alkyl (meth)acrylates, from 2% to 50% by weight of fatty-chain allyl ether of formula (I), and from 0% to 1% by weight of a crosslinking agent which is a well-known copolymerizable unsaturated polyethylenic monomer, for instance diallyl phthalate, allyl (meth)acrylate, divinylbenzene, (poly)ethylene glycol dimethacrylate or methylenebisacrylamide.

Among the latter polymers, those most particularly preferred are crosslinked terpolymers of methacrylic acid, of ethyl acrylate and of polyethylene glycol (10 EO) stearyl ether (Steareth-10), in particular those sold by the company Allied Colloids under the names Salcare SC 80® and Salcare SC 90®, which are aqueous 30% emulsions of a crosslinked terpolymer of methacrylic acid, of ethyl acrylate and of steareth-10 allyl ether (40/50/10).

(II) those comprising at least one hydrophilic unit of unsaturated olefinic carboxylic acid type, and at least one hydrophobic unit of $(C_{10}-C_{30})$alkyl ester of unsaturated carboxylic acid type.

Preferably, these polymers are selected from the group consisting of those in which the hydrophilic unit of unsaturated olefinic carboxylic acid type corresponds to the monomer of formula (II) below:

$$CH_2=\underset{\underset{R_1}{|}}{C}-\underset{\underset{O}{\|}}{C}-OH \quad \text{(II)}$$

in which $R_1$ denotes H or $CH_3$ or $C_2H_5$, that is to say acrylic acid, methacrylic acid or ethacrylic acid units, and in which the hydrophobic unit of $(C_{10}-C_{30})$alkyl ester of unsaturated carboxylic acid type corresponds to the monomer of formula (III) below:

$$CH_2=\underset{\underset{R_2}{|}}{C}-\underset{\underset{O}{\|}}{C}-OR_3 \quad \text{(III)}$$

in which $R_2$ denotes H or $CH_3$ or $C_2H_5$ (that is to say acrylate, methacrylate or ethacrylate units) and preferably H (acrylate units) or $CH_3$ (methacrylate units), $R_3$ denoting a $C_1O-C_{30}$ and preferably $C_{12}-C_{22}$ alkyl radical.

$(C_{10}-C_{30})$ alkyl esters of unsaturated carboxylic acids according to the invention include, for example, lauryl acrylate, stearyl acrylate, decyl acrylate, isodecyl acrylate and dodecyl acrylate, and the corresponding methacrylates, lauryl methacrylate, stearyl methacrylate, decyl methacrylate, isodecyl methacrylate and dodecyl methacrylate.

Anionic polymers of this type are described and prepared, for example, according to U.S. Pat. Nos. 3,915,921 and 4,509,949.

Among the anionic associative polymers of this type that will be used more particularly are polymers formed from a monomer mixture comprising:

(i) essentially acrylic acid, (ii) an ester of formula (III) described above in which $R_2$ denotes H or $CH_3$, $R_3$ denoting an alkyl radical containing from 12 to 22 carbon atoms, (iii) and a crosslinking agent, which is a well-known copolymerizable polyethylenic unsaturated monomer, for instance diallyl phthalate, allyl (meth)acrylate, divinylbenzene, (poly)ethylene glycol dimethacrylate and methylenebisacrylamide.

Among anionic associative polymers of this type that will be used more particularly are those consisting of from 95% to 60% by weight of acrylic acid (hydrophilic unit), 4% to 40% by weight of $C_{10}$–$C_{30}$ alkyl acrylate (hydrophobic unit) and 0% to 6% by weight of crosslinking polymerizable monomer, or alternatively those consisting of from 98% to 96% by weight of acrylic acid (hydrophilic unit), 1% to 4% by weight of $C_1O$—$C_{30}$ alkyl acrylate (hydrophobic unit) and 0.1% to 0.6% by weight of crosslinking polymerizable monomer such as those described above.

Among the said above polymers, those most particularly preferred according to the present invention are the products sold by the company Goodrich under the trade names Pemulen TR1®, Pemulen TR2® and Carbopol 1382®, and even more preferentially Pemulen TR1®, and the product sold by the company SEPPIC under the name Coatex SX®.

(III) maleic anhydride/$C_{30}$–$C_{38}$ α-olefin/alkyl maleate terpolymers, such as the product (maleic anhydride/$C_{30}$–$C_{38}$ α-olefin/isopropyl maleate copolymer) sold under the name Performa V 1608® by the company Newphase Technologies.

(IV) acrylic terpolymers comprising:

(a) about 20% to 70% by weight of a carboxylic acid containing α,β-monoethylenic unsaturation, (b) about 20% to 80% by weight of a non-surfactant monomer containing α,β-monoethylenic unsaturation other than (a), (c) about 0.5% to 60% by weight of a nonionic monourethane which is the product of reaction of a monohydric surfactant with a monoisocyanate containing monoethylenic unsaturation, such as those described in patent application EP-A-0 173 109 and more particularly the terpolymer described in Example 3, namely a methacrylic acid/methyl acrylate/behenyl dimethyl-meta-isopropenylbenzylisocyanate ethoxylated (40 EO) terpolymer, as an aqueous 25% dispersion.

(V) copolymers comprising among their monomers a carboxylic acid containing α,β-monoethylenic unsaturation and an ester of a carboxylic acid containing α,β-monoethylenic unsaturation and of an oxyalkylenated fatty alcohol.

Preferentially, these compounds also comprise as monomer an ester of a carboxylic acid containing α,-monoethylenic unsaturation and of a $C_1$–$C_4$ alcohol.

An example of a compound of this type which may be mentioned is Aculyn 22® sold by the company Rohm & Haas, which is a methacrylic acid/ethyl acrylate/stearyl methacrylate oxyalkylenated terpolymer.

Associative polymers of cationic type

Among these, mention may be made of:

(I) the cationic associative polyurethanes whose family has been described by the Applicant in French patent application No. 0 009 609; they may be represented by the general formula (Ia) below:

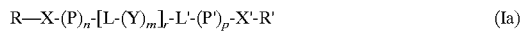

$$R—X-(P)_n-[L-(Y)_m]_r-L'-(P')_p-X'-R' \qquad (Ia)$$

in which:

R and R', which may be identical or different, represent a hydrophobic group or a hydrogen atom;

X and X', which may be identical or different, represent a group comprising an amine function optionally bearing a hydrophobic group, or alternatively a group L";

L, L' and L", which may be identical or different, represent a group derived from a diisocyanate;

P and P', which may be identical or different, represent a group comprising an amine function optionally bearing a hydrophobic group;

Y represents a hydrophilic group;

r is an integer between 1 and 100, preferably between 1 and 50 and in particular between 1 and 25, n, m and p each range, independently of each other, from 0 to 1000;

the molecule containing at least one protonated or quaternized amine function and at least one hydrophobic group.

In one preferred embodiment of these polyurethanes, the only hydrophobic groups are the groups R and R' at the chain ends.

One preferred family of cationic associative polyurethanes is the one corresponding to formula (Ia) described above and in which:

R and R' both independently represent a hydrophobic group,

X and X' each represent a group L", n and p are between 1 and 1000, and

L, L', L", P, P', Y and m have the meaning given above.

Another preferred family of cationic associative polyurethanes is the one corresponding to formula (Ia) above in which:

R and R'both independently represent a hydrophobic group, X and X' each represent a group L', n and p are 0, and L, L', L", Y and m have the meaning given above.

The fact that n and p are 0 means that these polymers do not comprise units derived from a monomer containing an amine function, incorporated into the polymer during the polycondensation. The protonated amine functions of these polyurethanes result from the hydrolysis of excess isocyanate functions, at the chain end, followed by alkylation of the primary amine functions formed with alkylating agents containing a hydrophobic group, i.e. compounds of the type RQ or R' Q, in which R and R' are as defined above and Q denotes a leaving group such as a halide, a sulphate, etc.

Yet another preferred family of cationic associative polyurethanes is the one corresponding to formula (Ia) above in which:

R and R' both independently represent a hydrophobic group,

X and X' both independently represent a group comprising a quaternary amine, n and p are 0, and L, L', Y and m have the meaning given above.

The number-average molecular mass of the cationic associative polyurethanes is preferably between 400 and 500 000, in particular between 1000 and 400 000 and ideally between 1000 and 300 000.

The expression "hydrophobic group" means a radical or polymer containing a saturated or unsaturated, linear or branched hydrocarbon-based chain, which may contain one or more hetero atoms such as P, 0, N or S, or a radical containing a perfluoro or silicone chain. When the hydrophobic group denotes a hydrocarbon-based radical, it comprises at least 10 carbon atoms, preferably from 10 to 30 carbon atoms, in particular from 12 to 30 carbon atoms and more preferably from 18 to 30 carbon atoms.

Preferentially, the hydrocarbon-based group is derived from a monofunctional compound.

By way of example, the hydrophobic group may be derived from a fatty alcohol such as stearyl alcohol, dodecyl alcohol or decyl alcohol. It may also denote a hydrocarbon-based polymer such as, for example, polybutadiene.

When X and/or X' denote(s) a group comprising a tertiary or quaternary amine, X and/or X' may represent one of the following formulae:

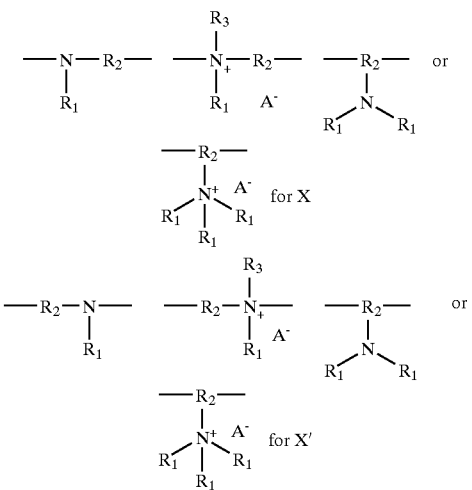

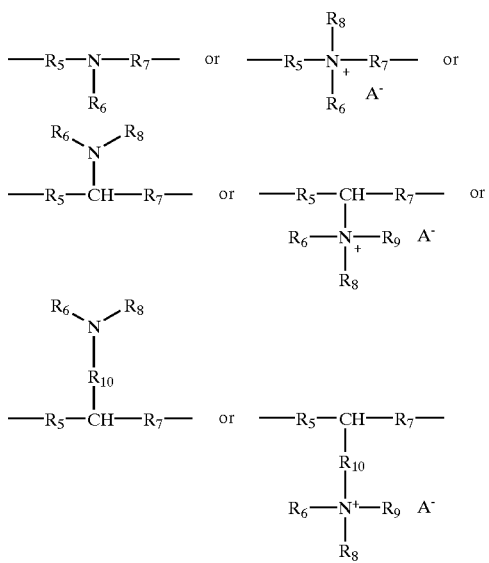

in which:

$R_2$ represents a linear or branched alkylene radical containing from 1 to 20 carbon atoms, optionally comprising a saturated or unsaturated ring, or an arylene radical, one or more of the carbon atoms possibly being replaced with a hetero atom selected from the group consisting of N, S, 0 and P;

$R_1$ and $R_3$, which may be identical or different, denote a linear or branched $C_1$–$C_{30}$ alkyl or alkenyl radical or an aryl radical, at least one of the carbon atoms possibly being replaced with a hetero atom selected from the group consisting of N, S, 0 and P;

$A^{31}$ is a physiologically acceptable counter-ion.

The groups L, L' and L" represent a group of formula:

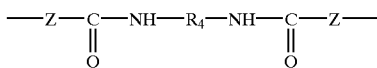

in which:

Z represents —O—, —S— or —NH—; and $R_4$ represents a linear or branched alkylene radical containing from 1 to 20 carbon atoms, optionally comprising a saturated or unsaturated ring or an arylene radical, one or more of the carbon atoms possibly being replaced with a hetero atom selected from the group consisting of N, S, 0 and P.

The groups P and P' comprising an amine function may represent at least one of the following formulae:

in which:

$R_5$ and $R_7$ have the same meanings as $R_2$ defined above;

$R_6$, $R_8$ and $R_9$ have the same meanings as $R_1$ and $R_3$ defined above;

$R_{10}$ represents a linear or branched, optionally unsaturated alkylene group which may contain one or more hetero atoms selected from the group consisting of N, 0, S and P, and $A^-$ is a physiologically acceptable counter-ion.

As regards the meaning of Y, the term "hydrophilic group" means a polymeric or non-polymeric water-soluble group.

By way of example, when it is not a polymer, mention may be made of ethylene glycol, diethylene glycol and propylene glycol.

When it is a hydrophilic polymer, in accordance with one preferred embodiment, mention may be made, for example, of polyethers, sulphonated polyesters, sulphonated polyamides or a mixture of these polymers. The hydrophilic compound is preferentially a polyether and in particular a poly(ethylene oxide) or poly(propylene oxide).

The cationic associative polyurethanes of formula (Ia) according to the invention are formed from diisocyanates and from various compounds with functions containing labile hydrogen. The functions containing labile hydrogen may be alcohol, primary or secondary amine or thiol functions giving, after reaction with the diisocyanate functions, polyurethanes, polyureas and polythioureas, respectively. The term "polyurethanes" in the present invention encompasses these three types of polymer, namely polyurethanes per se, polyureas and polythioureas, and also copolymers thereof.

A first type of compound involved in the preparation of the polyurethane of formula (Ia) is a compound comprising at least one unit containing an amine function. This compound may be multifunctional, but the compound is preferentially difunctional, that is to say that, according to one preferential embodiment, this compound comprises two labile hydrogen atoms borne, for example, by a hydroxyl, primary amine, secondary amine or thiol function. A mixture of multifunctional and difunctional compounds in which the percentage of multifunctional compounds is low may also be used.

As mentioned above, this compound may comprise more than one unit containing an amine function. In this case, it is a polymer bearing a repetition of the unit containing an amine function.

Compounds of this type may be represented by one of the following formulae:

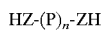

HZ-(P)$_n$-ZH or

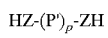

HZ-(P')$_p$-ZH in which Z, P, P', n and p are as defined above.

Examples of compounds containing an amine function that may be mentioned include N-methyldiethanolamine, N-tert-butyldiethanolamine and N-sulphoethyldiethanolamine.

The second compound involved in the preparation of the polyurethane of formula (Ia) is a diisocyanate corresponding to the formula:

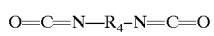

O=C=N—R$_4$-N=C=O in which R$_4$ is as defined above.

By way of example, mention may be made of methylenediphenyl diisocyanate, methylenecyclohexane diisocyanate, isophorone diisocyanate, toluene diisocyanate, naphthalene diisocyanate, butane diisocyanate and hexane diisocyanate.

A third compound involved in the preparation of the polyurethane of formula (Ia) is a hydrophobic compound intended to form the terminal hydrophobic groups of the polymer of formula (Ia).

This compound consists of a hydrophobic group and of a function containing a labile hydrogen, for example a hydroxyl, primary or secondary amine, or thiol function.

By way of example, this compound may be a fatty alcohol such as, in particular, stearyl alcohol, dodecyl alcohol or decyl alcohol. When this compound comprises a polymeric chain, it may be, for example, -hydroxylated hydrogenated polybutadiene.

The hydrophobic group of the polyurethane of formula (Ia) may also result from the quaternization reaction of the tertiary amine of the compound comprising at least one tertiary amine unit. Thus, the hydrophobic group is introduced via the quaternizing agent. This quaternizing agent is a compound of the type RQ or R'Q, in which R and R'are as defined above and Q denotes a leaving group such as a halide, a sulphate, etc.

The cationic associative polyurethane may also comprise a hydrophilic block. This block is provided by a fourth type of compound involved in the preparation of the polymer. This compound may be multifunctional. It is preferably difunctional. It is also possible to have a mixture in which the percentage of multifunctional compound is low.

The functions containing a labile hydrogen are alcohol, primary or secondary amine or thiol functions. This compound may be a polymer terminated at the chain ends with one of these functions containing a labile hydrogen.

By way of example, when it is not a polymer, mention may be made of ethylene glycol, diethylene glycol and propylene glycol.

When it is a hydrophilic polymer, mention may be made, for example, of polyethers, sulphonated polyesters and sulphonated polyamides, or a mixture of these polymers. The hydrophilic compound is preferentially a polyether and especially a poly(ethylene oxide) or poly(propylene oxide).

The hydrophilic group termed Y in formula (Ia) is optional. Specifically, the units containing a quaternary amine or protonated function may suffice to provide the solubility or water-dispersibility required for this type of polymer in an aqueous solution. Although the presence of a hydrophilic group Y is optional, cationic associative polyurethanes comprising such a group are, however, preferred.

(II) quaternized cellulose derivatives and polyacrylates containing non-cyclic amino side groups.

The quaternized cellulose derivatives are in particular:

quatemized celluloses modified with groups comprising at least one fatty chain, such as alkyl, arylalkyl or alkylaryl groups comprising at least 8 carbon atoms, or mixtures thereof;

quaternized hydroxyethylcelluloses modified with groups comprising at least one fatty chain, such as alkyl, arylalkyl or alkylaryl groups comprising at least 8 carbon atoms, or mixtures thereof The alkyl radicals borne by the above quaternized celluloses or hydroxyethylcelluloses preferably comprise from 8 to 30 carbon atoms. The aryl radicals preferably denote phenyl, benzyl, naphthyl or anthryl groups.

Examples of quaternized alkylhydroxyethylcelluloses containing $C_8$–$C_{30}$ fatty chains that may be mentioned include the products Quatrisoft LM 200®, Quatrisoft LM-X 529-18-A®, Quatrisoft LM-X 529-18B® ($C_{12}$ alkyl) and Quatrisoft LM-X 529-8® ($C_{18}$ alkyl) sold by the company Amerchol and the products Crodacel QM®, Crodacel QL® ($C_{12}$ alkyl) and Crodacel QS® ($C_{18}$ alkyl) sold by the company Croda.

Amphoteric associative polymers

These are preferably selected from the group consisting of polymers comprising at least one non-cyclic cationic unit. Even more particularly, the ones that are preferred are those prepared from or comprising 1 to 20 mol% of monomer comprising a fatty chain, preferably 1.5 to 15 mol% and even more particularly 1.5 to 6 mol%, relative to the total number of moles of monomers.

The amphoteric associative polymers that are preferred according to the invention comprise, or are prepared by copolymerizing:

1) at least one monomer of formula (Ia) or (Ib):

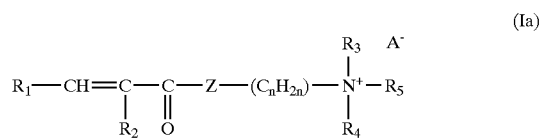

(Ia)

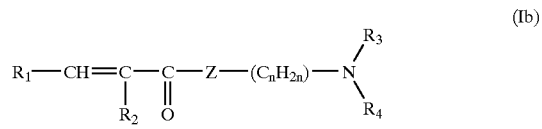

(Ib)

in which R$_1$ and R$_2$, which may be identical or different, represent a hydrogen atom or a methyl radical, R$_3$, R$_4$ and R$_5$, which may be identical or different, represent a linear or branched alkyl radical containing from 1 to 30 carbon atoms, Z represents an NH group or an oxygen atom, n is an integer from 2 to 5, A$^-$ is an anion derived from an organic or mineral acid, such as a methosulphate anion or a halide such as chloride or bromide;

2) at least one monomer of formula (II)

R$_6$—CH=CR$_7$—COOH (II)

in which R$_6$ and R$_7$, which may be identical or different, represent a hydrogen atom or a methyl radical;

and 3) at least one monomer of formula (III):

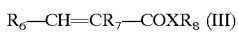

$R_6$—CH=$CR_7$—$COXR_8$ (III)

in which $R_6$ and $R_7$, which may be identical or different, represent a hydrogen atom or a methyl radical, X denotes an oxygen or nitrogen atom and $R_8$ denotes a linear or branched alkyl radical containing from 1 to 30 carbon atoms;

at least one of the monomers of formula (Ia), (Ib) or (III) comprising at least one fatty chain.

The monomers of formulae (Ia) and (Ib) of the present invention are preferably selected from the group consisting of the group consisting of:

dimethylaminoethyl methacrylate, dimethylaminoethyl acrylate, diethylaminoethyl methacrylate, diethylaminoethyl acrylate, dimethylaminopropyl methacrylate, dimethylaminopropyl acrylate, dimethylaminopropylmethacrylamide, dimethylaminopropylacrylamide, these monomers optionally being quatemized, for example with a $C_1$–$C_4$ alkyl halide or a $C_1$–$C_4$ dialkyl sulphate.

More particularly, the monomer of formula (Ia) is selected from the group consisting of acrylamidopropyltrimethylammonium chloride and methacrylamidopropyltrimethylammonium chloride.

The monomers of formula (II) of the present invention are preferably selected from the group consisting of the group consisting of acrylic acid, methacrylic acid, crotonic acid and 2-methylcrotonic acid. More particularly, the monomer of formula (II) is acrylic acid.

The monomers of formula (III) of the present invention are preferably selected from the group consisting of the group consisting of $C_{12}$–$C_{22}$ and more particularly $C_{16}$–$C_{18}$ alkyl acrylates or methacrylates.

The monomers constituting the fatty-chain amphoteric polymers of the invention are preferably already neutralized and/or quaternized.

The ratio of the number of cationic charges/anionic charges is preferably equal to about 1.

The amphoteric associative polymers according to the invention preferably comprise from 1 mol% to 10 mol% of the monomer comprising a fatty chain (monomer of formula (Ia), (Ib) or (III)), and preferably from 1.5 mol% to 6 mol%.

The weight-average molecular weights of the amphoteric associative polymers according to the invention may range from 500 to 50 000 000 and are preferably between 10 000 and 5 000 000.

The amphoteric associative polymers according to the invention may also contain other monomers such as nonionic monomers and in particular such as $C_1$–$C_4$ alkyl acrylates or methacrylates.

Amphoteric associative polymers according to the invention are described and prepared, for example, in patent application WO 98/44012.

Among the amphoteric associative polymers according to the invention, the ones that are preferred are acrylic acid/(meth)acrylamidopropyltrimethylammonium chloride/stearyl methacrylate terpolymers.

Associative polymers of nonionic type

According to the invention, these are preferably selected from the group consisting of:

(1) celluloses modified with groups comprising at least one fatty chain;

examples that may be mentioned include:

hydroxyethylcelluloses modified with groups comprising at least one fatty chain, such as alkyl, arylalkyl or alkylaryl groups, or mixtures thereof, and in which the alkyl groups are preferably $C_8$–$C_{22}$, for instance the product Natrosol Plus Grade 330 CS® ($C_{16}$ alkyls) sold by the company Aqualon, or the product Bermocoll EHM 100® sold by the company Berol Nobel, those modified with alkylphenyl polyalkylene glycol ether groups, such as the product Amercell Polymer HM-1500® (nonylphenyl polyethylene glycol (15) ether) sold by the company Amerchol.

(2) hydroxypropyl guars modified with groups comprising at least one fatty chain, such as the product Esaflor HM 22® ($C_{22}$ alkyl chain) sold by the company Lamberti, and the products RE210-18® ($C_{14}$ alkyl chain) and RE205-1 ($C_{20}$ alkyl chain) sold by the company Rhône-Poulenc.

(3) copolymers of vinylpyrrolidone and of fatty-chain hydrophobic monomers; examples that may be mentioned include:

the products Antaron V216® or Ganex V216® (vinylpyrrolidone/hexadecene copolymer) sold by the company I.S.P.

the products Antaron V220® or Ganex V220® (vinylpyrrolidone/eicosene copolymer) sold by the company I.S.P.

(4) copolymers of $C_1$–$C_6$ alkyl methacrylates or acrylates and of amphiphilic monomers comprising at least one fatty chain, such as, for example, the oxyethylenated methyl acrylate/stearyl acrylate copolymer sold by the company Goldschmidt under the name Antil 208®.

(5) copolymers of hydrophilic methacrylates or acrylates and of hydrophobic monomers comprising at least one fatty chain, such as, for example, the polyethylene glycol methacrylate/lauryl methacrylate copolymer.

(6) polyurethane polyethers comprising in their chain both hydrophilic blocks usually of polyoxyethylenated nature and hydrophobic blocks which may be aliphatic sequences alone and/or cycloaliphatic and/or aromatic sequences.

(7) polymers with an aminoplast ether skeleton containing at least one fatty chain, such as the Pure Thix® compounds sold by the company Sud-Chemie.

Preferably, the polyurethane polyethers comprise at least two hydrocarbon-based lipophilic chains containing from 6 to 30 carbon atoms, separated by a hydrophilic block, the hydrocarbon-based chains possibly being pendent chains, or chains at the end of the hydrophilic block. In particular, it is possible for one or more pendent chains to be included. In addition, the polymer may comprise a hydrocarbon-based chain at one end or at both ends of a hydrophilic block.

The polyurethane polyethers may be multiblock, in particular in triblock form. Hydrophobic blocks may be at each end of the chain (for example: triblock copolymer with a hydrophilic central block) or distributed both at the ends and in the chain (for example: multiblock copolymer). These same polymers may also be graft polymers or starburst polymers.

The nonionic fatty-chain polyurethane polyethers may be triblock copolymers in which the hydrophilic block is a polyoxyethylenated chain comprising from 50 to 1 000 oxyethylene groups. The nonionic polyurethane polyethers comprise a urethane linkage between the hydrophilic blocks, whence arises the name.

By extension, also included among the nonionic fatty-chain polyurethane polyethers are those in which the hydrophilic blocks are linked to the lipophilic blocks via other chemical bonds.

As examples of nonionic fatty-chain polyurethane polyethers that may be used in the invention, mention may also be made of Rheolate 205® containing a urea function, sold by the company Rheox, or the Rheolates® 208, 204 or 212, and also Acrysol RM 184®.

Mention may also be made of the product Elfacos T210® containing a $C_{12-14}$ alkyl chain, and the product Elfacos T212® containing a $C_{18}$ alkyl chain, from Akzo.

The product DW 1206B® from Rohm & Haas containing a $C_{20}$ alkyl chain and a urethane linkage, sold at a solids content of 20% in water, may also be used.

It is also possible to use solutions or dispersions of these polymers, especially in water or in aqueous-alcoholic medium. Examples of such polymers that may be mentioned are Rheolate® 255, Rheolate® 278 and Rheolate® 244 sold by the company Rheox. The products DW 1206F and DW 1206J sold by the company Rohm & Haas may also be used.

The polyurethane polyethers that may be used according to the invention are in particular those described in the article by G. Fonnum, J. Bakke and Fk. Hansen—Colloid Polym. Sci 271, 380.389 (1993).

Even more particularly, according to the invention, it is preferred to use a polyurethane polyether that may be obtained by polycondensation of at least three compounds comprising (i) at least one polyethylene glycol comprising from 150 to 180 mol of ethylene oxide, (ii) stearyl alcohol or decyl alcohol, and (iii) at least one diisocyanate.

Such polyurethane polyethers are sold especially by the company Rohm & Haas under the names Aculyn 46® and Aculyn 44® [Aculyn 46® is a polycondensate of polyethylene glycol containing 150 or 180 mol of ethylene oxide, of stearyl alcohol and of methylenebis(4-cyclohexyl isocyanate) (SMDI), at 15% by weight in a matrix of maltodextrin (4%) and water (81 %); Aculyn 44® is a polycondensate of polyethylene glycol containing 150 or 180 mol of ethylene oxide, of decyl alcohol and of methylenebis(4-cyclohexylisocyanate) (SMDI), at 35% by weight in a mixture of propylene glycol (39%) and water (26%)].

Medium

The medium, for the dye composition, which is suitable for dyeing is preferably an aqueous medium consisting of water possibly advantageously comprising cosmetically acceptable organic solvents including, more particularly, alcohols or diols such as ethyl alcohol, isopropyl alcohol, hexyleneglycol (2-methyl 2,4-pentanediol), neopentylglycol, 3-methyl-1,5-pentanediol, benzyl alcohol and phenylethyl alcohol, or glycols or glycol ethers such as, for example, ethylene glycol monomethyl, monoethyl and monobutyl ether, propylene glycol or its ethers such as, for example, propylene glycol monomethyl ether, butylene glycol, dipropylene glycol, and also diethylene glycol alkyl ethers such as, for example, diethylene glycol monoethyl ether or monobutyl ether. The solvents may then be present, each in concentrations of between about 0.5% and 20% and preferably between about 2% and 10% by weight, relative to the total weight of the composition.

Other adjuvants

The dye composition according to the invention may also contain other agents, known previously elsewhere in oxidation dyeing, such as various common adjuvants, for instance sequestering agents such as EDTA and etidronic acid, UW screening agents, waxes, volatile or non-volatile, cyclic or linear or branched silicones, which are optionally organo-modified (in particular with amine groups), preserving agents, ceramides, pseudoceramides, plant, mineral or synthetic oils, vitamins or provitamins, for instance panthenol, opacifiers, etc.

The said composition may also contain reducing agents or antioxidants. These agents may be chosen in particular from sodium sulphite, thioglycolic acid, thiolactic acid, sodium bisulphite, dehydroascorbic acid, hydroquinone, 2-methylhydroquinone, tert-butylhydroquinone and homogentisic acid, and, in this case, they are generally present in amounts ranging from about 0.05% to 3% by weight relative to the total weight of the composition.

The dye composition according to the invention may also preferably comprise at least one additional fatty alcohol, these fatty alcohols being introduced in a pure form or in the form of a mixture. Among them, mention may be made more particularly of lauryl, cetyl, stearyl and oleyl alcohols and mixtures thereof. These additional fatty alcohols can represent from about 0.001% to 20% of the total weight of the composition.

Needless to say, a person skilled in the art will take care to select the optional additional compound(s) mentioned above such that the advantageous properties intrinsically associated with the ready-to-use composition according to the invention are not, or are not substantially, adversely affected by the envisaged addition(s).

Oxidizing agent

In the oxidizing composition, the oxidizing agent is preferably selected from the group consisting of hydrogen peroxide, urea peroxide, alkali metal bromates or ferricyanides, and persalts such as perborates and persulphates. It is particularly preferred to use hydrogen peroxide. This oxidizing agent advantageously consists of an aqueous hydrogen peroxide solution whose titre may range, more particularly, from about 1 to 40 volumes and even more preferably from about 5 to 40 volumes.

Oxidizing agents that may also be used are one or more redox enzymes such as laccases, peroxidases and 2-electron oxidoreductases (such as uricase), where appropriate in the presence of their respective donor or co-factor.

The pH of the ready-to-use composition applied to the keratin fibres [composition resulting from mixing together the dye composition and the oxidizing composition] is generally preferably between 3 and 12, limits included. It is preferably between 8.5 and 11, limits included, and may be adjusted to the desired value using acidifying or basifying agents that are well known in the prior art in the dyeing of keratin fibres.

Among the basifying agents which may be used, for example, are aqueous ammonia, alkali metal carbonates, alkanolamines such as monoethanolamine, diethanolamine and triethanolamine and derivatives thereof, oxyethylenated and/or oxypropylenated hydroxyalkylamines and ethylenediamines, sodium hydroxide, potassium hydroxide and the compounds of the following formula:

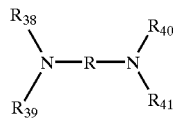

in which R is a propylene residue optionally substituted with a hydroxyl group or a $C_1-C_4$ alkyl radical; $R_{38}$, $R_{39}$, $R_{40}$ and $R_{41}$, which may be identical or different, represent a hydrogen atom, a $C_1-C_4$ alkyl radical or a $C_1-C_4$ hydroxyalkyl radical.

The acidifying agents are conventionally, for example, mineral or organic acids, for instance hydrochloric acid, orthophosphoric acid, carboxylic acids, for instance tartaric acid, citric acid or lactic acid, or sulphonic acids.

The dyeing process according to the invention preferably consists in applying the ready-to-use composition, prepared extemporaneously at the time of use from the dye composition and the oxidizing composition described above, to wet or dry keratin fibres, and in leaving the composition to act for an exposure time preferably ranging from 1 to 60 minutes approximately, and more preferably from 10 to 45 minutes approximately, in rinsing the fibres and then in optionally washing them with shampoo, then rinsing them again and drying them.

A concrete example illustrating the invention is given below without, however, being limiting in nature.

EXAMPLE 1

The following dye composition was prepared:
Colorant composition:
(expressed in grams of Active Substance)

| | |
|---|---|
| Carboxylic lauryl ether acid 4.5 EO (Akypo ® RLM 45 sold by Chem Y) | 7 |
| Lauryl alcohol 2 EO (Dehydrol ® LS-2-DEO-N sold by Cognis) | 4 |
| Decyl alcohol 5 EO (Empilan ® KA-5/90-FL sold by Albright & Wilson) | 8 |
| Oleyl alcohol | 3 |
| Carboxylic (C13/C15)alkyl ether acid monoethanolamide containing 2 mol of ethylene oxide | 5 |
| Nonionic associative polymer (Dapral ® T212 sold by Akzo) | 1 |
| Monoethanolamine | 2 |
| Polyquaternium 6 (Merquat ® 100 sold by Calgon) | 1.5 |
| Ethanol | 11 |
| Propylene glycol | 5 |
| Dipropylene glycol | 5 |
| 1,3-Dihydroxybenzene (resorcinol) | 0.3 |
| para-Phenylenediamine | 0.3 |
| Reducing agents, antioxidants | qs |
| Sequestering agent | qs |
| Fragrance | qs |
| Aqueous ammonia (containing 20.5% ammonia) | 1.6 |
| Demineralized water   qs | 100 |

At the time of use, the colorant composition was mixed, in a plastic bowl and for 2 minutes, with an oxidizing composition assaying 20-volume hydrogen peroxide in the proportion or 1 part colorant composition per 1.5 parts oxidizing composition.

The mixture obtained was applied on 90% white locks of hair and left on for 30 minutes.

The locks then were rinsed with water, they were washed with shampoo, rinsed again with water, then dried and combed out.

A greenish-brown shade then was obtained.

EXAMPLE 2

On a préparé la composition de teinture suivante
Composition colorante:
(exprimee en grammes de Matiere active)

| | |
|---|---|
| Alcoyl C12 éther de glycérol (1.5 moles) | 4 |
| hexyléne glycol (2 methyl-2,4 pentanediol) | 5 |
| Alcool éthylique 96 degrés dénature | 9 |
| Acide lauryl éther carboxylique (4.5 OE) | 8 |
| Amide d'acides de colza oxyéthyléné (4 OE) | 6 |
| Alcool oléique | 2 |
| Lauryl hydroxyethylcellulose quaternisée | 1 |
| Alcool decylique oxyéthyléne (5 OE) | 6 |
| Thiolactate d'ammonium en solution aqueuse à 58% (50% en acide thiolactique) | 0.8 |
| Polycondensat tétraméthyl hexaméthylénediamine/ dichloro 1,3-propyléne en solution aqueuse | 2 |

| -continued | |
|---|---|
| 3-méthyl-1-phényl-5-pyrazolone | 0.15 |
| 1,3-dihydroxybenzéne (resorcinol) | 0.056 |
| 1-hydroxy-3-amino-benzéne | 0.31 |
| 1,4-diamino-benzéne | 0.4 |
| Acide éthyléne diamine tétracétique | 0.2 |
| Monoéthanolamine pure | 1.1 |
| Acide érythorbique (ou acide d-isoascorbique) | 0.12 |
| Parfum | 0.7 |
| Ammoniaque (concentration de référence à 20%) | 8 |
| Dipropyléne glycol | 6 |
| Eau desionisée | Qsp 100 |

La composition colorante a été mélangée, au moment de l'emploi, dans un bol en plastique et pendant 2 minutes, à une composition oxydante titrant 20 volumes en eau oxygénée à raison de 1 partie de composition colorante pour 1,5 partie de composition oxydante.

On a appliqué le mélange obtenu sur des méches de cheveux à 90% de blancs et on a laissé poser 30 minutes.

On a ensuite rincé les méches à l'eau, on les a lavées au shampooing, à nouveau rincées a l'eau, puis séchées et démêlées.

On a obtenu alors une nuance brun verdâtre.

In view of the above description of the invention one of ordinary skill in the art is now able to both make and use a composition for the oxidation dyeing of keratin fibres, in particular of human keratin fibres and more particularly the hair, comprising, preferably in a medium that is suitable for dyeing, at least one oxidation dye, characterized in that it also comprises at least one polyoxyalkylenated carboxylic acid ether or a salt thereof, at least one nonionic surfactant and at least one cationic or amphoteric polymer whose cationic charge density is greater than or equal to 2 meq/gram, as well as a ready-to-use composition for the oxidation dyeing of keratin fibres, in particular of human keratin fibres such as the hair, characterized in that it is obtained by mixing a dye composition as defined herein and an oxidizing composition comprising at least one oxidizing agent, as well as a process for dyeing keratin fibres, in particular for human keratin fibres and more particularly the hair, characterized in applying to the fibres at least one dye composition comprising, preferably in a medium that is suitable for dyeing, at least one oxidation dye, the colour being developed at alkaline, neutral or acidic pH using an oxidizing composition comprising, in a medium that is suitable for dyeing, at least one oxidizing agent, which is mixed with the dye composition just at the time of use, or which is applied sequentially without intermediate rinsing, the dye composition and the oxidizing composition also comprising, distributed indifferently between the two, at least one polyoxyalkylenated carboxylic acid ether or a salt thereof, at least one nonionic surfactant and at least one cationic or amphoteric polymer whose cationic charge density is greater than or equal to 2 meq/gram, as well as a process for dyeing keratin fibres, in particular for human keratin fibres and more particularly the hair, characterized in applying to the fibres at least one dye composition comprising, preferably in a medium that is suitable for dyeing, at least one oxidation dye, the colour being developed at alkaline, neutral or acidic pH using an oxidizing composition comprising, in a medium that is suitable for dyeing, at least one oxidizing agent, which is mixed with the dye composition just at the time of use, or which is applied sequentially without intermediate rinsing, the dye composition or the oxidizing composition also comprising, combined in the same composition, at least one polyoxyalkylenated carboxylic acid ether or a salt thereof, at least one nonionic surfactant and at least one cationic or amphoteric polymer whose cationic charge density is greater than or equal to 2 meq/gram, as well as a multi-compartment device or "kit" for dyeing human keratin fibres and more particularly the hair, characterized in that at least one compartment contains a dye composition comprising, in a medium that is suitable for dyeing, at least one oxidation dye, and in that another compartment contains an oxidizing composition comprising, in a medium that is suitable for dyeing, an oxidizing agent, the dye composition and the oxidizing composition also comprising, distributed indifferently between the two, at least one polyoxyalkylenated carboxylic acid ether or a salt thereof, at least one nonionic surfactant and at least one cationic or amphoteric polymer whose cationic charge density is greater than or equal to 2 meq/gram and a multi-compartment device or "kit" for dyeing human keratin fibres and more particularly the hair, characterized in that at least one compartment contains a dye composition comprising, in a medium that is suitable for dyeing, at least one oxidation dye, and in that another compartment contains an oxidizing composition comprising, in a medium that is suitable for dyeing, an oxidizing agent, the dye composition or the oxidizing composition also comprising, combined in the same composition, at least one polyoxyalkylenated carboxylic acid ether or a salt thereof, at least one nonionic surfactant and at least one cationic or amphoteric polymer whose cationic charge density is greater than or equal to 2 meq/gram. In a similar fashion, one of ordinary skill is now able to make and use a composition comprising at least one oxidation dye, at least one polyoxyalkylenated carboxylic acid ether or a salt thereof, at least one nonionic surfactant, and at least one cationic or amphoteric polymer whose cationic charge density is greater than or equal to 2 meq/gram.

All references, documents, texts, patents, applications, product literature, articles, etc. mentioned herein are incorporated by reference herein, as is French patent application 0116738 filed Dec. 21, 2001, priority to which is hereby claimed. Where a numericl range or limit is described herein, all values and subranges falling therewithin are expressly included as if specifically written out.

What is claimed is:

1. A composition comprising at least one oxidation dye, at least one polyoxyalkylenated carboxylic acid ether or a salt thereof, at least one nonionic surfactant, and at least one cationic or amphoteric polymer whose cationic charge density is greater than or equal to 2 meq/gram.

2. A composition according to claim 1, comprising a polyoxyalkylenated carboxylic acid ether or salt thereof having formula (I):

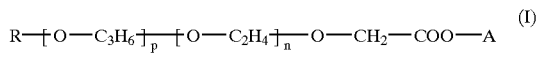

in which:
R represents a linear or branched $C_8$–$C_{22}$ alkyl or alkenyl radical, a ($C_8$–$C_9$)alkylphenyl radical or a radical R'CONH-$CH_2$—$CH_2$- with R' denoting a linear or branched $C_{11}$–$C_{21}$ alkyl or alkenyl radical,
n is an integer or fraction ranging from 2 to 24,
p is an integer or fraction ranging from 0 to 6,
A denotes a hydrogen atom or Na, K, Li, 1/2Mg or a monoethanolamine, ammonium or triethanolamine residue.

3. A composition according to claim 2, wherein, in formula (I), R denotes a ($C_{12}$)alkyl radical, A denotes a hydrogen or sodium atom, p=0 and n ranges from 2 to 10.

4. A composition according to claim 1, wherein the at least one nonionic surfactant is selected from the group consisting of alcohols, alpha-diols, polyethoxylated or polypropoxylated alkylphenols having a fatty chain containing from 8 to 22 carbon atoms, the number of ethylene oxide or propylene oxide groups ranging from 1 to 50; copolymers of ethylene and propylene oxide; condensates of ethylene and propylene oxide with fatty alcohols; polyethoxylated fatty amides having from 2 to 30 mol of ethylene oxide; mono- or polyglycerolated fatty alcohols containing 1 to 30 glycerol groups and polyglycerolated fatty amides containing 1 to 5 glycerol groups; oxyethylenated fatty acid esters of sorbitan having from 2 to 30 mol of ethylene oxide; fatty acid esters of sucrose; fatty acid esters of polyethylene glycol; alkyl polyglycosides; N-alkylglucamine derivatives; oxides of alkyl ($C_{10}$–$C_{14}$)amines and oxides of N-acylaminopropylmorpholine.

5. A composition according to claim 4, wherein the at least one nonionic surfactant is selected from the group consisting of:
1) fatty alcohols containing from 8 to 22 carbon atoms and oxyethylenated with 1 to 10 mol of ethylene oxide,
2) mono- or polyglycerolated fatty alcohols of formula (II) below:

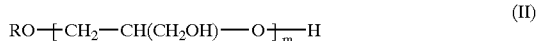

in which:
R represents a saturated or unsaturated, linear or branched radical containing from 8 to 40 carbon atoms;
m represents a number ranging from 1 to 30.

6. A composition according to claim 5, comprising a mono- or polyglycerolated fatty alcohol of formula (II) selected from the group consisting of the $C_8$/$C_{10}$ alcohol containing one mole of glycerol, the $C_{10}$/$C_{12}$ alcohol containing 1 mol of glycerol and the $C_{12}$ alcohol containing 1.5 mol of glycerol.

7. A composition according to claim 1, wherein the at least one cationic or amphoteric polymer having a cationic charge density greater than or equal to 2 meq/gram is selected from the group consisting of:
1) quaternary polymers of vinylpyrrolidone and of vinylimidazole
2) homopolymers of dimethyldiallylammonium chloride
3) -copolymers of dimethyldiallylammonium chloride and acrylamide
4) -copolymers of acrylic acid and dimethyldiallylammonium
5) -quaternary diammonium polymers comprising units of formula (V) below:

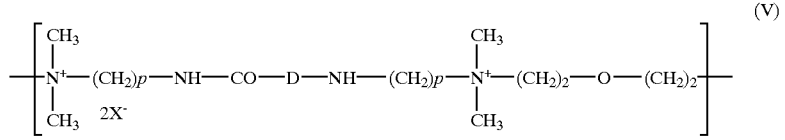

in which:

p denotes an integer varying from about 1 to 6,

D may be zero or may represent a group —(CH$_2$)r—CO— in which r denotes a number equal to 4 or to 7, and X$^-$ is an anion, and 6)-quaternary diammonium polymers comprising repeating units of formula (IV)a below:

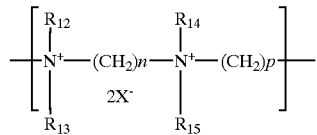

(IV)a in which $R_{12}$, $R_{13}$, $R_{14}$ and $R_{15}$, which are identical or different, denote an alkyl or hydroxyalkyl radical having from about 1 to 4 carbon atoms, n and p are integers varying from 2 to 20.

8. A composition according to claim 7, comprising a compound of formula (V), p is equal to 3, and is selected from the group consisting of:

a) D represents a group —(CH$_2$)$_4$—CO—, X denotes a chlorine atom, b) D represents a group —(CH$_2$)$_7$—CO—, X denotes a chlorine atom, c) D denotes the value zero, X denotes a chlorine atom, and d) a block copolymer formed of units corresponding to the polymers described in paragraphs a) and c).

9. A composition according to claim 7, comprising a compound of formula (IV)a, where $R_{12}$, $R_{13}$, $R_{14}$ and $R_{15}$ represent a methyl radical and n=3, p=6 and X=Cl, or alternatively $R_{12}$ and $R_{13}$ represent a methyl radical, $R_{14}$ and $R_{15}$ represent an ethyl radical and n=p=3 and X=Br.

10. A composition according to claim 1, wherein the polyoxyalkylenated carboxylic acid ethers or salts thereof represent 2% to 15% by weight relative to the total weight of the composition.

11. A composition according to claim 1, wherein the nonionic surfactants represent 2% to 40% by weight relative to the total weight of the composition.

12. A composition according to claim 1, wherein the cationic or amphoteric polymers having a cationic charge density >2 meq/gram represent 0.01% to 10% by weight relative to the total weight of the composition.

13. A composition according to claim 1, wherein the oxidation dye is selected from the group consisting of oxidation bases and couplers.

14. A composition according to claim 13, wherein it comprises at least one oxidation base.

15. A composition according to claim 14, wherein the oxidation base is selected from the group consisting of ortho- or para-phenylenediamines, double bases, ortho- or para-aminophenols, heterocyclic bases, and salts thereof.

16. A composition according to claim 15, comprising a para-phenylenediamine selected from the group consisting of the compounds of formula (VII) below:

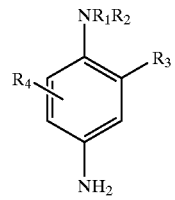

(VII)

in which:

R1 represents a hydrogen atom, a C1–C4 alkyl radical, a C1–C4 monohydroxyalkyl radical, a C2–C4 polyhydroxyalkyl radical, a (C1–C4)alkoxy(C1–C4)alkyl radical or a C1–C4 alkyl radical substituted with a nitrogenous, phenyl or 4'-aminophenyl group;

R2 represents a hydrogen atom, a C1–C4 alkyl radical, a C1–C4 monohydroxyalkyl radical, a C2–C4 polyhydroxyalkyl radical, a (C1–C4)alkoxy(C1–C4)alkyl radical or a C1–C4 alkyl radical substituted with a nitrogenous group;

R1 and R2 may also form, with the nitrogen atom that bears them, a 5- or 6-membered nitrogen heterocycle optionally substituted with one or more alkyl, hydroxyl or ureido groups;

R3 represents a hydrogen atom, a halogen atom, a C1–C4 alkyl radical, a sulpho radical, a carboxyl radical, a C1–C4 monohydroxyalkyl radical, a C1–C4 hydroxyalkoxy radical, an acetylamino(C1–C4)alkoxy radical, a mesylamino(C1–C4)alkoxy radical or a carbamoylamino(C 1–C4)alkoxy radical, R4 represents a hydrogen or halogen atom or a C1–C4 alkyl radical.

17. A composition according to claim 15, comprising a double base selected from the group consisting of compounds of structure (VIII) below:

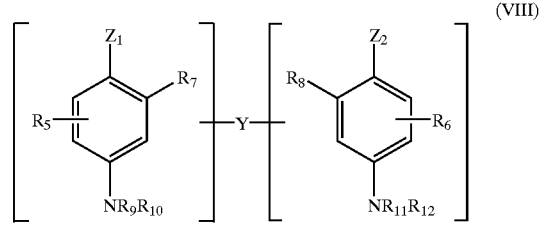

(VIII)

in which:

Z, and Z$_2$, which may be identical or different, represent a hydroxyl or -NH2 radical which may be substituted with a C$_1$–C$_4$ alkyl radical or with a linker arm Y;

the linker arm Y represents a linear or branched alkylene chain containing from 1 to 14 carbon atoms, which may be interrupted by or terminated with one or more nitrogenous groups and/or one or more hetero atoms such as oxygen, sulphur or nitrogen atoms, and optionally substituted with one or more hydroxyl or Cl-C$_6$ alkoxy radicals;

R$_5$ and R6 represent a hydrogen or halogen atom, a C$_1$–C$_4$ alkyl radical, a C$_1$–C$_4$ monohydroxyalkyl radical, a C$_2$–C$_4$ polyhydroxyalkyl radical, a C1–C$_4$ aminoalkyl radical or a linker arm Y;

R$_7$, R$_8$, R$_9$, R$_{10}$, R$_{11}$ and R$_{12}$, which may be identical or different, represent a hydrogen atom, a linker arm Y or a C$_1$–C$_4$ alkyl radical;

wherein the compounds of formula (VIII) contain only one linker arm Y per molecule.

18. A composition according to claim 16, wherein the nitrogenous group is selected from the group consisting of amino, mono($C_1$–$C_4$)alkylamino, di($C_1$–$C_4$)alkylamino, tri ($C_1$–$C_4$)alkylamino, monohydroxy($C_1$–$C_4$)alkylamino, imidazolinium and ammonium radicals.

19. A composition according to claim 15, comprising a para-aminophenols selected from the group consisting of compounds of structure (IX):

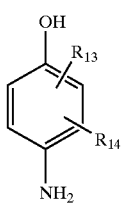

(IX)

in which:

$R_{13}$ represents a hydrogen atom, a halogen atom, or a $C_1$–$C_4$ alkyl, $C_1$–$C_4$ monohydroxyalkyl, ($C_1$–$C_4$) alkoxy($C_1$–$C_4$)alkyl, $C_1$–$C_4$ aminoalkyl or hydroxy ($C_1$–$C_4$)alkylamino($C_1$–$C_4$)alkyl radical, $R_{14}$ represents a hydrogen atom, a halogen atom, or a $C_1$–$C_4$-alkyl, $C_1$–$C_4$ monohydroxyalkyl, $C_2$–$C_4$ polyhydroxyalkyl, Cl-$C_4$ aminoalkyl, $C_1$–$C_4$ cyanoalkyl or ($C_1$–$C_4$)alkoxy($C_1$–$C_4$)alkyl radical.

20. A composition according to claim 15, comprising a heterocyclic base selected from the group consisting of pyridines, pyrimidines, and pyrazoles.

21. A composition according to claim 13, comprising an oxidation base in an amount of 0.0005% to 12% by weight relative to the total weight of the composition.

22. A composition according to claim 13, comprising a coupler selected from the group consisting of meta-phenylenediamines, meta-aminophenols, meta-diphenols, heterocyclic couplers, and acid addition salts thereof.

23. A composition according to claim 13, comprising a coupler, wherein the coupler is present in an amount of 0.0001% to 10% relative to the total weight of the composition.

24. A composition according to claim 15, wherein the salts are selected from the group consisting of hydrochlorides, hydrobromides, sulphates, tartrates, lactates and acetates.

25. A composition according to claim 1, further comprising at least one direct dye.

26. A composition according to claim 1, further comprising at least one reducing agent in an amount of 0.05% to 3% by weight relative to the total weight of the composition.

27. A composition according to claim 1, further comprising at least one additional fatty alcohol in an amount by weight of 0.001% to 20% relative to the total weight of the composition.

28. A composition according to claim 1, further comprising at least one associative polymer in an amount of 0.01% to 10% relative to the total weight of the composition.

29. A ready-to-use composition obtained by mixing a dye composition as defined in claim 1 and an oxidizing composition comprising at least one oxidizing agent.

30. A composition according to claim 29, wherein the oxidizing agent comprises a compound selected from the group consisting of hydrogen peroxide, urea peroxide, alkali metal bromates or ferricyanides, persalts, redox enzymes, peroxidases and 2-electron oxidoreductases.

31. A composition according to claim 30, comprising hydrogen peroxide.

32. A composition according to claim 31, comprising an aqueous hydrogen peroxide solution whose titre ranges from 1 to 40 volumes.

33. A composition according to claim 1, wherein it has a pH ranging from 3 to 12.

34. A composition according to claim 29, wherein the polyoxyalkylenated carboxylic acid ethers or salts thereof are present in an amount of 0.5% to 15% by weight relative to the total weight of the composition.

35. A composition according to claim 29, wherein the nonionic surfactants are present in an amount of 0.5% to 40% by weight relative to the total weight of the composition.

36. A composition according to claim 29, wherein the cationic or amphoteric polymers having a cationic charge density >2 meq/gram are present in an amount of 0.0025% to 10% relative to the total weight of the composition.

37. A process for dyeing keratin fibres comprising applying to the fibres at least one dye composition comprising, in a medium that is suitable for dyeing, at least one oxidation dye, the colour being developed at alkaline, neutral or acidic pH using an oxidizing composition comprising, in a medium that is suitable for dyeing, at least one oxidizing agent, which is mixed with the dye composition just at the time of use, or which is applied sequentially without intermediate rinsing, the dye composition and the oxidizing composition also comprising, distributed in any manner between the two, at least one polyoxyalkylenated carboxylic acid ether or a salt thereof, at least one nonionic surfactant and at least one cationic or amphoteric polymer whose cationic charge density is greater than or equal to 2 meq/gram.

38. A process for dyeing keratin fibres as claimed in claim 37, comprising applying to the fibres at least one dye composition comprising, in a medium that is suitable for dyeing, at least one oxidation dye, the colour being developed at alkaline, neutral or acidic pH using an oxidizing composition comprising, in a medium that is suitable for dyeing, at least one oxidizing agent, which is mixed with the dye composition just at the time of use, or which is applied sequentially without intermediate rinsing, the dye composition or the oxidizing composition also comprising, combined in the same composition, at least one polyoxyalkylenated carboxylic acid ether or a salt thereof, at least one nonionic surfactant and at least one cationic or amphoteric polymer whose cationic charge density is greater than or equal to 2 meq/gram.

39. A process according to claim 37, comprising applying the ready-to-use composition, prepared extemporaneously at the time of use from the dye composition and the oxidizing composition, to wet or dry keratin fibres, and leaving the composition to act for an exposure time ranging from about 1 to 60 minutes, rinsing the fibres and optionally washing them with shampoo, rinsing them again and drying them.

40. A multi-compartment device or kit for dyeing human keratin fibres, wherein said kit comprises at least one compartment having a dye composition therein comprising, at least one oxidation dye, and in another compartment having an oxidizing composition comprising an oxidizing agent, the dye composition and the oxidizing composition also comprising, distributed in any manner between the two, at least one polyoxyalkylenated carboxylic acid ether or a salt thereof, at least one nonionic surfactant and at least one cationic or amphoteric polymer whose cationic charge density is greater than or equal to 2 meq/gram.

41. The multi-compartment device or kit for dyeing human keratin fibres according to claim 40, the dye composition or the oxidizing composition comprising, combined in the same composition, at least one polyoxyalkylenated carboxylic acid ether or a salt thereof, at least one nonionic surfactant and at least one cationic or amphoteric polymer whose cationic charge density is greater than or equal to 2 meq/gram.

* * * * *

UNITED STATES PATENT AND TRADEMARK OFFICE
CERTIFICATE OF CORRECTION

PATENT NO. : 6,692,539 B2
DATED : February 17, 2004
INVENTOR(S) : Patricia Desenne et al.

It is certified that error appears in the above-identified patent and that said Letters Patent is hereby corrected as shown below:

Column 30,
Line 50, "Z," should read -- $Z_1$ --.

Signed and Sealed this

Sixth Day of July, 2004

JON W. DUDAS
*Acting Director of the United States Patent and Trademark Office*